United States Patent
Drobnitzky

(10) Patent No.: US 7,787,676 B2
(45) Date of Patent: Aug. 31, 2010

(54) METHOD FOR INTEGRATION OF VECTORIAL AND/OR TENSORIAL MEASUREMENT DATA INTO A REPRESENTATION OF AN ANATOMICAL IMAGE EXPOSURE

(75) Inventor: Matthias Drobnitzky, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 1000 days.

(21) Appl. No.: 11/406,574

(22) Filed: Apr. 18, 2006

(65) Prior Publication Data

US 2006/0262968 A1  Nov. 23, 2006

(30) Foreign Application Priority Data

Apr. 18, 2005  (DE) ............... 10 2005 017 850

(51) Int. Cl.
*G06K 9/00* (2006.01)
*G06F 3/033* (2006.01)
*G06F 3/048* (2006.01)

(52) U.S. Cl. ............... 382/128; 382/130; 382/131; 382/132; 345/157; 715/856; 715/857; 715/859; 715/860; 715/861; 715/862

(58) Field of Classification Search ............... 382/128, 382/130, 131, 132; 345/157; 715/856, 857, 715/858, 859, 860, 861, 862
See application file for complete search history.

(56) References Cited

U.S. PATENT DOCUMENTS

| | | | | |
|---|---|---|---|---|
| 4,217,642 A | * | 8/1980 | Dam et al. ............... | 600/526 |
| 5,657,050 A | * | 8/1997 | McCambridge et al. ...... | 715/856 |
| 5,682,489 A | * | 10/1997 | Harrow et al. ............... | 715/839 |
| 5,686,938 A | * | 11/1997 | Batkhan ............... | 715/861 |
| 6,049,622 A | | 4/2000 | Robb et al. | |
| 6,867,790 B1 | * | 3/2005 | Brooks ............... | 715/856 |
| 7,154,453 B2 | * | 12/2006 | Numano ............... | 345/1.1 |
| 7,202,851 B2 | * | 4/2007 | Cunningham et al. ....... | 345/156 |
| 7,293,246 B2 | * | 11/2007 | Baudisch et al. ............ | 715/858 |
| 2002/0111757 A1 | | 8/2002 | Boehler et al. | |
| 2002/0173721 A1 | | 11/2002 | Grunwald et al. | |
| 2002/0176614 A1 | | 11/2002 | Kuth et al. | |
| 2004/0064036 A1 | | 4/2004 | Mao et al. | |
| 2004/0106916 A1 | * | 6/2004 | Quaid et al. ............... | 606/1 |
| 2005/0209525 A1 | * | 9/2005 | Bojovic et al. ............... | 600/512 |

FOREIGN PATENT DOCUMENTS

WO   WO 02/056240   7/2002

OTHER PUBLICATIONS

Lécuyer, Anatole, Jean-Marie Burkhardt, and Laurent Etienne. "Feeling bumps and holes without a haptic interface: the perception of pseudo-haptic textures." Proceedings of the SIGCHI conference on Human factors in computing systems (2004): 239-246. Print.*

* cited by examiner

*Primary Examiner*—Matthew C Bella
*Assistant Examiner*—Michael A Newman
(74) *Attorney, Agent, or Firm*—Schiff Hardin LLP

(57) ABSTRACT

In a method for integration of vectorial and/or tensorial measurement data into a representation on a screen of an anatomical image exposure acquired with an imaging medical examination apparatus, upon and/or after selection of, and/or upon and/or after sweeping over, image points of the anatomical representation by means of a screen representation that is associated with at least one control tool operable by a user, the screen representation and/or the speed of movement of the screen representation is varied dependent on the direction information provided by the measurement data.

16 Claims, 2 Drawing Sheets

METHOD FOR INTEGRATION OF VECTORIAL AND/OR TENSORIAL MEASUREMENT DATA INTO A REPRESENTATION OF AN ANATOMICAL IMAGE EXPOSURE

BACKGROUND OF THE INVENTION

1. Field of the Invention

The present invention concerns a method for integration of vectorial and/or tensorial measurement data into a representation on a screen of an anatomical image exposure acquired with an imaging medical examination apparatus.

2. Description of the Prior Art

With medical measurement techniques, for example magnetic resonance tomography, it is possible to determine different spatially-resolved characteristics of an examination subject, such as, for example, tissue characteristics. External influences such as a contrast agent administration or applied mechanical oscillations can additionally be used for this purpose in order, for example, to determine tissue elasticity or reflexivity.

To represent such measurement values in connection with the associated anatomical structures, it has previously been typical to generate an anatomical representation in grey values, on which anatomical representation a color-coded parameter image is then superimposed. Examples of such a representation are the false-color representation of active areas in the human cortex that is superimposed on an anatomical brain image, or red- and blue-color-coded flow images for differentiation of venous and arterial blood that are superimposed on a vessel representation. Representations known as perfusion maps from stroke diagnostics (supported by magnetic resonance apparatuses) are similarly superimposed on diffusion-weighted representations of the brain.

To make such a representation possible, it is necessary for the measurement value to be represented is a scalar, so that it can be associated with a color value. In cases in which the additional measurement value that transcends the purely anatomical data is multi-dimensional, it is necessary to resort to auxiliary constructions such as a representation of vector arrows or the like, but inevitably only a part of the actual present information can be reproduced. The conventionally-used vector arrows thus are shown only for a few selected points of the anatomical representation, such that ultimately a large part (the majority) of the actual measurement information is lost in the representation.

SUMMARY OF THE INVENTION

An object of the present invention is to provide a method for integrating vectorial and/or tensorial measurement data into a display screen representation of an anatomical image exposure, wherein the aforementioned problems associated with known methods are avoided.

This object, is achieved in accordance with the invention by a method of the aforementioned type, upon and/or after selection of and/or upon and/or after sweeping over, image points of the anatomical representation by means of a screen representation that is associated with at least one control tool that can be operated by a user, the screen display and/or the speed of a movement of the screen display is varied dependent on the direction information provided by the measurement data.

The anatomical image exposure (for example a brain image or a vessel representation) thus is shown to the user on a monitor or display or other image output means, with the user having the possibility to use a control tool that cause movement of a corresponding screen representation to be displaced (shifted). By means of a user-controlled movement of the control tool, all image points or pixels of the anatomical representation can be swept over by the associated screen representation of the tool. Alternatively or simultaneously, a selection of individual image points or a group of multiple image points can ensue that an appropriate selection function that is provided by the control tool is used.

The image point-related measurement data (such as, for example, the tissue elasticity) that are present with regard to the anatomical image are used in order to modify the screen representation associated with the control tool and/or the speed with which this screen representation is moved, such that the user can infer from the change (which is a measure for the underlying data information) the measurement data that are associated with the corresponding local region of the anatomical representation.

For each individual image point of the anatomical representation, the user thus obtains information with regard to the local existing measurement values thereof. Depending on the type of the alteration of the screen representation or type of the screen representation itself, multi-dimensional measurement data thus can be made perceptible. The information provided in the inventive method via the active direction of the control tool by the user can be perceived better by making actively-accessed information intuitively discernable and remembered, better than the conventional case of represented information for a number of regions in which the user is not necessarily interested.

The modification of the screen representation of the user is dependent on the locally-present measurement data tensor or vector, while the variation of the movement speed of the screen representation communicates to the user a haptic-type experience, so that the user receives the feeling that, for example, a resistance exists in an swept-over region or at a point, this resistance being greater or smaller dependent on the region or point, or depending on the movement speed. For example, elevations and depressions of the anatomical representation can be emphasized, or a transition between various friction types can be made perceptible. By means of the inventive method, a manual palpation can be virtually emulated, for example even in regions in which an actual palpation is not possible. The inventive method can likewise be helpful in order to plan an operation in which a feeling for the section hardness in the given region or for specific anatomical characteristics is communicated to the user by the speed change. Use in the training field is also relevant in this context, for example to allow an operation to initially be practiced using the inventive method and using a model.

For different vectorial or tensorial measurement data (that, for example, correspond to different mechanical characteristics), it is appropriate to select different conversions for the alteration of the screen representation or the speed modification. The spatial dependence on measurement data in the sense of a depth or height of a surface thus can be determined via a speed change with different accelerations. The acceleration can be set proportional to the depth or height of the surface, such that the speed is correspondingly reduced given an increase, so the acceleration is constant given a movement in the plane, and increases given a decline downwards. Given a friction on tissue, the movement can be speed-dependent in the sense that, given a transition from static friction to dynamic friction, a sudden speed increase ensues upon crossing a limit speed of the movement implemented by the user.

In accordance with the invention a computer mouse and/or a joystick and/or a touchpad and/or a keyboard can be used as a control tool. A computer mouse as well as a keyboard is present at nearly all current-used data processing systems that are used in connection with the visualization of image data, so that no retrofitting (upgrading) is necessary. Further control tools that, if applicable, are less distributed or are used only for special applications can naturally also be used in the framework of the inventive method.

It is important for at least one selection or one sweep over image points of a representation to be made with the control tool. It can be advantageous to have available different selection types or movement types that, for example, are provided by the multiple buttons of a computer mouse or by the multiple buttons of a joystick. A number of selection types thus can be differentiated as needed, by which a different modification of screen representation or of the speed of the movement of the same can be achieved, for example with regard to different measurement data sets that have been acquired. By a selection via a click with the left mouse button, the user can signal that a change of the screen representation to be effected should ensue dependent on measurement data for the proton density while a click with the right mouse button or the middle mouse button can relate to present data regarding relaxation times or flow speeds. Given the use of a number of control tools, the measurement data to be integrated into the representation depend on the currently-actuated control tool.

An arrow that can be varied in terms of its direction and/or length can be used as a screen representation associated with the control tool. This arrow can exhibit a basic shape as it is used as an arrow for a mouse pointer or a pointer for a joystick or the like. More specific arrow types can be used, for example colored arrows or arrows with particular line features or specific arrowheads. The printing direction of the arrow can be changed dependent on the direction information of the vectorial or, respectively, tensorial measurement data, for example dependent on the direction (provided by measurement data) of the most significant (strongest) diffusion. The length of the arrow similarly can be reduced or enlarged in order to indicate that, for example, a particularly stronger flow of blood or of another fluid is occurring in the specified direction, or that a flow is hindered, for example due to an interfering vessel deposit. Color coding can additionally or alternatively be used in order to direct the user to an underlying critical measurement value. It is normally possible to use blue arrows; but for a particularly weak or strong flow or an otherwise abnormal measurement datum, it is possible to change the color of the arrow representation, for example to red. If the user now sweeps over the anatomical image that shows a measure for the spatially-dependent distribution of at least one fundamental, measured, mechanical characteristic, the screen representation in the form of the arrow thus changes according to the underlying quantity.

Furthermore, an icon can be inventively provided (in particular an icon that can be varied in terms of its form (shape)) as a screen representation associated with the control tool. The icon can be selected such that it symbolizes the measurement quantity or characteristic to be represented, for example a wave symbol as an indicator of the vectorial measurement quantity "flow direction". If time-dependent data are used as measurement data, a cursor symbol or another symbol of comparably simple design can also be used. The icon can be varied in terms of its form (for example by blinking) in order to direct the attention of the user to the icon, or it indicate the magnitude or the direction of the associated measurement datum by its form.

A representation of a of a multi-dimensional object that can be varied in terms of its alignment and/or magnitude and/or magnitude relationships can be used as a screen representation associated with the control tool. The use of a multi-dimensional object allows conclusions about various vector components to be ascertainable for the user given vectorial measurement data with a single representation. For example, a real two-dimensional representation on a screen can be used that includes an x-component and a y-component corresponding to the x-value and y-value of a vectorial measurement datum. Higher-dimensional objects can be represented in perspective or using special 3D techniques and the like. Depending on the image point swept over or selected and dependent on the type of the selection, the alignment, the magnitude or the magnitude relationships (for example the ratio of various axes to one another), and therewith the shape, can be changed depending on how the individual components of the underlying measurement data are designed, or dependent on which measurement quantity should be represented.

The multi-dimensional object can be an ellipse and/or an ellipsoid and/or a circle and/or a sphere and/or a rectangle and/or a cuboid. In these subjects, the respective axis or the boundary lines with their individual points (which, if applicable, have different intervals from the center point of the respective object) can be a measure for the measurement datum in the respective direction. It is naturally also possible to use the different dimensions of the subject to communicate (impart) different measurement data; for example, a two-dimensional representation plane can thus be used to specify the preferred diffusion direction in the plane, while a third dimension, for example, specifies the magnitude of the relaxivity of a shown tissue.

Furthermore, in accordance with the invention a representation of a region of the anatomical image exposure associated with the selected and/or swept-over image point is used as the control tool. For example, it is possible to repeatedly show a small region around the swept-over or selected image point or the pixel in sections, if applicable enlarged, in order to give the user a better orientation. It is also possible to make the surrounding data (which are often influential given vectorial measurement data) more easily perceivable for the user by a targeted, exaggerated or distorted representation of the surroundings, for example by a specific lightening or darkening which the observer associates with elevations and depressions.

The screen representation and/or the speed of a movement of the screen representation can be varied dependent on actual or virtual forces acting on an anatomical region that is associated with selected and/or swept-over image points and/or forces emanating from this region, in particular forces occurring in the framework of an elastography, measurement and/or palpation. For example, in real-time elastography ultrasound exposures can be produced that are acquired under various tissue compressions. Hard tissue regions deform less significantly (severely) than soft tissue regions, such that the tissue hardness can be identified from the associated measurement data. The screen representation or the movement of the screen representation can now be altered dependent on such acting forces that are actually applied in a measurement or on merely visualized forces, for example given a virtual palpation. Given a selection of an image point, it is thus possible to significantly shorten or to extend a screen representation (such as a mouse pointer) in order to simulate a large influence on the acting forces, while a small alteration is selected for a slight or only lightly-acting influence. The speed of a movement can likewise be significantly changed in order, for example, to clarify the inertia or the friction force between a tissue (for example in the brain) and a virtual object moving over the tissue or an anatomical region of another type. For example, the effects of pressure or shear forces that can either be actually acting or derived from present measurement data, can thus be made perceivable to the user.

The screen representation associated with the control tool furthermore can be altered by changing the representation location. For example, it is thus possible for the mouse pointer to "jumps back" given a mouse click in specific regions of the image in order to represent an evasion (sidestep; avoidance) of the shown anatomical structure to the side. Such an evasion to the side can, for example, occur given a pressure acting from above. The direction of the "jump back" is used as a measure for the direction of the evasion, while the magnitude of the spatial variation (thus, for example, the extent of the "jump back") represents a measure for the strength of the evasion of, for example, a tissue structure. It is likewise possible that the screen representation (thus, for example, an icon) does not follow the path (track) predetermined by the user upon sweeping over a specific image point or a specific image point region, but rather appears to the side of this path in order to indicate the displacement capability of an anatomical structure, for example given the effect of a lateral pressure. The amount of this lateral deviation thereby specifies a measure for the intensity of the present displacement capability.

Moreover, the direction of the speed of the movement of the screen representation associated with the control tool can be varied. For example, when the user moves the control tool upwards, a variation of the representation can actually ensue by a displacement in a lateral direction or even downwards. The user thereby receives the feeling that he or she moves over a small rise (hill) or a barrier in the anatomical structure, for example a lymph node or a tumor, the size or shape of which is made perceivable by the speed change upon sweeping over a region containing the tumor or a region containing the node.

The alteration of the screen representation upon and/or after selection of image points of the anatomical representation can inventively ensue continuously and/or in steps. For example, given selection of a specific image point a relaxation of the tissue there (if applicable under inclusion of adjacent tissue structures) can be shown by varying the screen representation (which is, for example, associated with a computer mouse), varies in steps. For example, a representation of a region of the anatomical image exposure can initially be shown given the effect of a pressure force and then in individual exposures given a slow relaxation of the tissue. Alternatively, a relaxation can also be shown continuously. The alteration can also occur, if applicable, by a repeated movement at the site in order, for example, to show an underlying pumping process.

The speed of the alteration of the screen representation can be varied dependent on the vectorial and/or tensorial measurement data, in particular dependent on the magnitude of an associated measurement datum. For example, a shown icon or an arrow can move particularly quickly in a specific direction, for example in order to clarify that a preferred diffusion direction is very strongly pronounced. By contrast, a slow movement in this direction can clarify for the user that, although the preferred diffusion or also the flow direction is situated here, this is not strongly distinguished relative to the other directions.

According to the invention, tissue characteristics, in particular the proton density, relaxation times, flow speeds, flow directions, the BOLD effect, the chemical shift, the magnetization transfer, the diffusion, the perfusion, the relaxivity and/or the elasticity can be used as vectorial and/or tensorial measurement data. These measurement quantities can be determined, for example, spatially-resolved with magnetic resonance apparatuses. If applicable, additional external influences due to contrast agent administration or applied mechanical oscillations are also required in order, for example, to determine the relaxivity and elasticity. For example, given use of other measurement techniques further characteristics can naturally also be used that can be associated with any anatomical structures. It is only decisive that the characteristics can be linked with an anatomical image exposure that is shown on a screen or can be associated with this. If the integration of preceding, exemplarily known tissue characteristics allows an experience in the tactile range in order, for example, to replace a real, non-implementable palpation of a tissue to be understood in the broadest sense, the use of further characteristics can thus impart auxiliary or background information. For example, measurement data of physiological processes or of environmental conditions present during the examination can also be incorporated.

The anatomical image exposure can be acquired by a magnetic resonance apparatus or a computed tomography apparatus and/or an x-ray apparatus or an ultrasound apparatus or a camera apparatus or a scanner apparatus. In general, all imaging methods that exist in the medical field can be used for generation of the anatomical image exposure, insofar as the measurement data can be associated with sufficient precision. It can be advantageous to produce the anatomical image exposure was produced with the same apparatus with which some or all measurement data were also acquired in order, if applicable, to achieve an easy association capability. It is also possible to acquire the measurement data with a medical apparatus that cannot be used for imaging. In such a case, the anatomical image exposure is inevitably to be acquired by another apparatus, for example a camera. The image exposure can also be acquired from exposures or data of various apparatuses.

With the inventive method it is possible to reproduce not only scalar but also vectorial or tensorial measurement data on a screen, such that the existing information can be recalled and recognized without problems by the user. By the corresponding adaptation of a screen representation that is associated with a control tool of the user, the measurement data can be made perceivable by the user so that he or she receives a direct, haptic impression of the associated anatomical structure. A simpler and better evaluation, and, if applicable, medical assessment (finding) of the existing data is possible than would be possible given evaluation of the underlying number values that cannot be intuitively comprehended.

DESCRIPTION OF THE PREFERRED EMBODIMENTS

Figure 1:
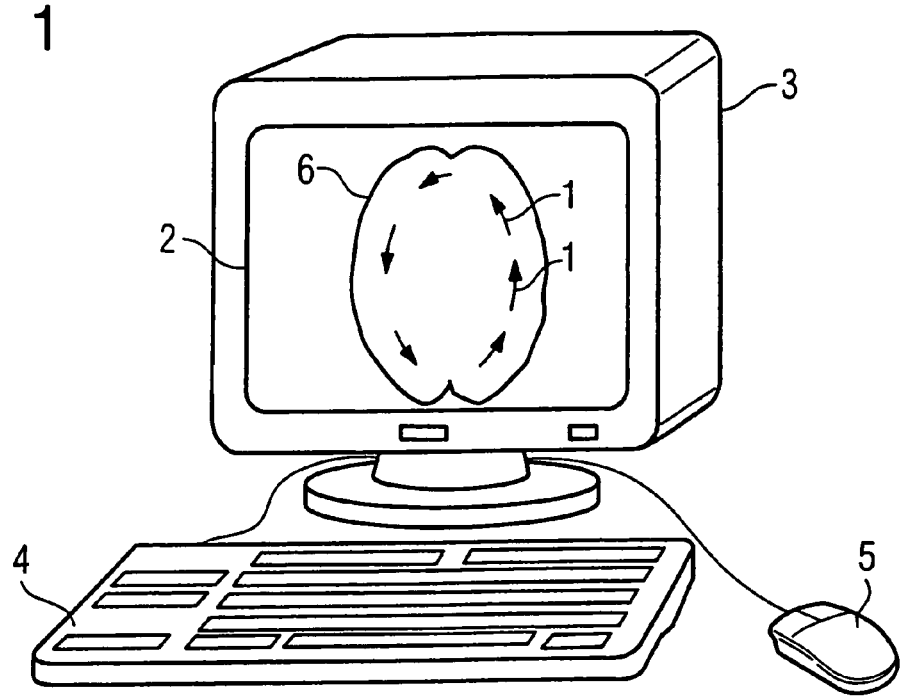
FIG. 1 shows the variation of an arrow-shaped screen representation upon sweeping over image points in the inventive method.

FIG. 1 shows the variation of an arrow-shaped screen representation 1 upon sweeping over image points in the inventive method. An acquired anatomical image exposure 2 is shown to a user on a screen 3 that is connected with a keyboard 4 as well as a computer mouse 5 via a computer (not shown here). The anatomical image exposure 2 shows a view of a human brain 6 that the user can sweep over image point-by-point using of both control tools in the form of keyboard 4 and a computer mouse 5.

An arrow-shaped screen representation 1 is associated with the keyboard 4 as well as the computer mouse 5, which screen representation 1 is dynamically altered dependent on the respective image point of the anatomical image exposure 2. The variation of the arrow-shaped screen representation 1 is shown for six different image points that the user has previously selected upon sweeping over the representation of the human brain 6, here via a click with the computer mouse 5. The individual, arrow-shaped screen representations 1 differ both in terms of their direction and in terms of their length in order to specify a preferred diffusion direction while a measure for the strength of the diffusion is simultaneously provided by the variation of the arrow length.

On the part of the user, or by means of a predetermined program, it can be set whether the various arrow-shaped screen representations 1 are displayed for a longer or a shorter time after selection of the image point. If applicable, an arrow-shaped screen representation 1 can remain until the user enacts a deletion of all screen representations 1. The user can likewise order that, after a specific number of created arrow-shaped screen representations 1, the first shown screen representations 1 are deleted and the like.

With the inventive method, the tensorial measurement datum that is provided by the diffusion is integrated without information loss into the representation of the anatomical image exposure 2 such that the user, given selection of an associated image point in the representation of the human brain 6, receives an indication of the corresponding measurement data that can be recognized at a glance.

Figure 2:
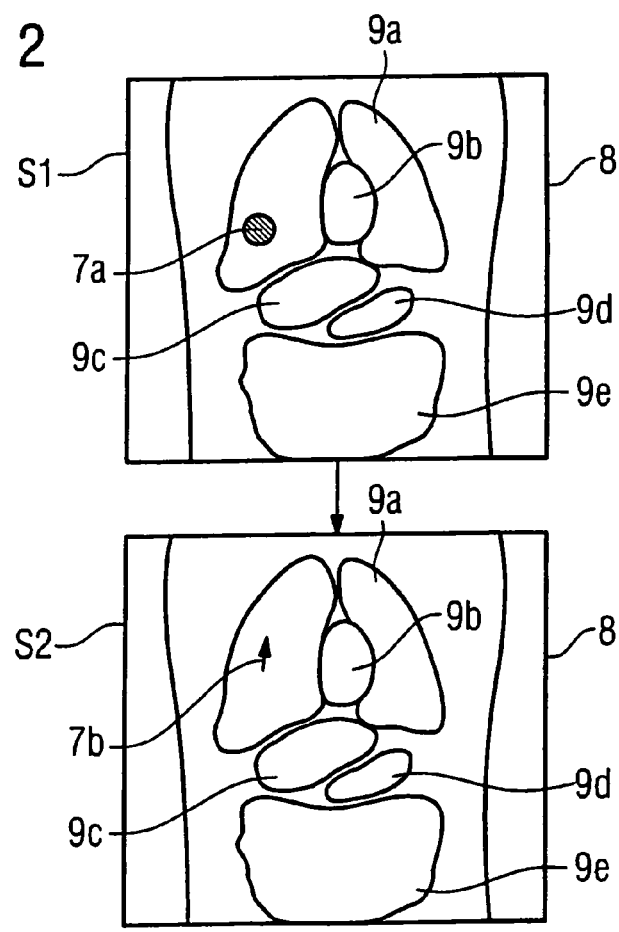
FIG. 2 shows the variation of the location and the type of a screen representation after selection of image points in the inventive method.

FIG. 2 shows a variation of the location and the type of a screen representation 7a, 7b after selection of image points in an inventive method. Furthermore, an anatomical representation 8 is shown that shows the torso of a person with the various organs 9a-9e.

In step S1, a user (not shown) selects an image point region in the lung 9a with the aid of the circular screen representation 7a which is associated with the user's control tool (not shown here). After selection (effected on the part of the user) of the image points of the anatomical representation 8 associated with the screen representation 7a, the representation location of the screen representation continuously varies, whereby the type of the screen representation (thus the displayed form) simultaneously changes.

A snapshot of this variation is shown in step S2. Here the screen representation 7b is an arrow pointing upwards (thus no longer a circle) that is additionally displaced upwards relative to the selection location that was indicated in step S1 by the screen representation 7a. The reaction of the tissue of the lung 9a that this would show given a manual palpation corresponding to a pressure exertion on the tissue is hereby made perceptible to the user. The length of the arrow and the magnitude of the variation of the representation location of the screen representation 7b relative to the original screen representation 7a represent a measure for the evasion of the tissue or, respectively, a measure for an exerted pressure force. Measurement results are thus made haptically perceivable to the user, for example in order to assess a lung fibrosis.

Further measurement data, for example for the elasticity of other organs or further tissue characteristics, can likewise be shown when the user sweeps over the other organs or, respectively, selects image points there or selects another selection type (such as, for example, a clicking of another mouse button) in the lung 9a.

Figure 3:
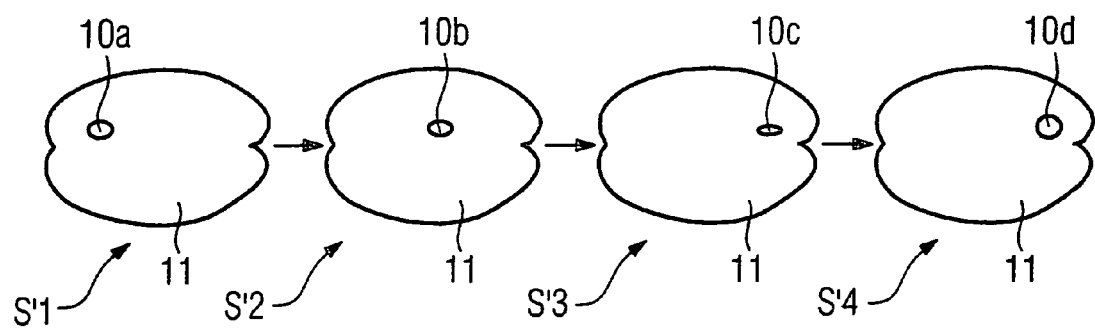
FIG. 3 shows the use of a variable, multi-dimensional object as a screen representation.

FIG. 3 shows the use of a variable, multi-dimensional object 10 as a screen representation. The multi-dimensional object 10 is an ellipsoid (shown simplified for representation purposes) that is associated with the various image points of an anatomical image exposure 11 of the human brain. In the steps S'1 through S'4, the user sweeps over different image points of the anatomical image exposure 11 with the screen representation of the multi-dimensional object 10, whereby the multi-dimensional object 10 assumes the different ellipsoid shapes 10-10d. The ellipsoid shape from 10a to 10b, thus given movement in the anatomical image exposure 11 from left to right, is thereby initially flatter until the ellipsoid shape 10c (which is associated with the step S'3) is only a flat disc. By contrast, given a further movement downwards (as it is shown in step S'4) the ellipsoid shape 10d assumes a nearly spherical shape.

The ellipsoid shapes 10a-10d show the strength of the diffusion in the different spatial directions, whereby respectively the distance from the center point of the ellipsoid shape 10a-10d is a measure for the diffusion strength in the respective associated direction. The speed of the movement of the screen representation simultaneously changes upon sweeping over the anatomical image exposure 11, whereby surface structures about which measurement data are likewise present are made perceivable to the user. A speed increase of the speed of the movement of the control tool on the part of the user thereby imparts the impression of moving into a depression or recess of a structure, while a slowdown imparts the experience of a rise or hill.

Figure 4:
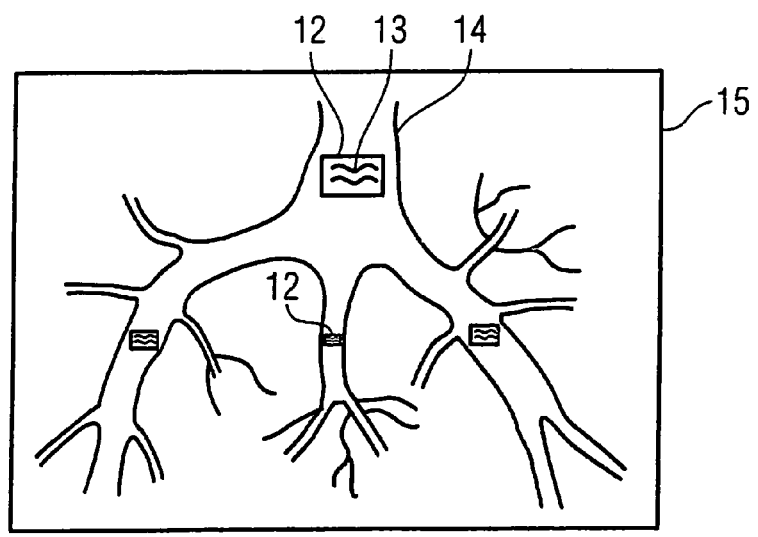
FIG. 4 shows the use of a variable icon as a screen representation in the inventive method.

FIG. 4 shows the use of a variable icon 12 as a screen representation in an inventive method. The icon 12 shows a flow symbol 13 that serves for representation of the blood flow in a vessel tree system 14. In the anatomical representation 15 of the vessel tree system 14, the user selects various image points in that he marks these with a control tool. An icon 12 with flow symbols 13 appears given selection of the marking type that is associated with the measurement data for the blood flow.

Given other selection types that are associated with other measurement data such as the relaxation or the like, other icons are shown to the user so that he or she immediately recognizes that qualitatively-different data are shown here.

Dependent on the respective selected point of the anatomical image exposure 15 of the vessel tree system 14, the icon 12 exhibits different sizes that represent the strength of the blood flow. The user thus can immediately detect when a disproportionally small flow predominates in a vessel, which indicates disruptions of the blood flow, for example due to deposits or thromboses.

Measurement data that are of a vectorial or tensorial type thus can be integrated into anatomical image exposures with the inventive method, whereby an "overloading" of the image with information on the one hand and an information loss due to gaps of the representation on the other hand are avoided. The doctor or medical-technical assistant who has the task of evaluation of the measurement data can experience an intuitive, "perceivable" representation of the given data.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for presenting an anatomic image exposure, composed of image points, to a viewer in a combined presentation with measurement data, comprising the steps of:

in a memory accessible by a computer, storing measurement data defining direction information respectively associated with said image points of said anatomical image exposure, said measurement being selected from the group consisting of vectorial measurement data and tensorial measurement data and being correlated in said memory with said image points;

at a display screen in communication with said computer, displaying a display representation of said anatomical image exposure that embodies display of said measurement data in said display representation correlated with said image points of said anatomical image exposure;

also displaying a screen representation of a manually-operable control tool on said display representation on said display screen and manually operating said control tool to perform an action with said screen representation of said control tool interacting with respective image points of said anatomical image in said display representation exposure, selected from the group consisting of selecting image points of said representation of said anatomical image exposure and sweeping over image points of said representation of said anatomical image exposure; and at a time selected from the group consisting of upon initiation of said action and after initiation of said action, automatically electronically producing a change, through said computer, in at least one of said screen representation of said control tool and speed of movement of screen representation of said control tool, that represents and corresponds to the direction information defined by the measurement data associated with the respective image points with which the tool interacts in said action, and through said change, imparting said representation of said measurement data, correlated with the respective image points, to a user who is manually operating said control tool to perform said action.

2. A method as claimed in claim 1 comprising employing as said control tool, a control tool selected from the group consisting of a computer mouse, a joystick, and a touch pad.

3. A method as claimed in claim 1 comprising displaying an arrow as said screen representation of said control tool, and wherein the step of varying at least one of said screen representation of said control tool and said speed of movement of said screen representation of said control tool comprises varying at least one of a direction and a length of said arrow.

4. A method as claimed in claim 1 comprising displaying a shape-variable icon as said screen representation of said control tool.

5. A method as claimed in claim 1 comprising displaying a multi-dimensional object as said screen representation of said control tool, and wherein the step of automatically electronically varying at least one of said screen representation of said control tool and a speed of movement of said screen representation of said control tool comprises varying at least one of an alignment of said multi-dimensional object on said display screen, a size of said multi-dimensional object on said display screen, and size ratios of respective dimensions of said multi-dimensional object on said display screen.

6. A method as claimed in claim 5 comprising displaying, as said multi-dimensional object, an object selected from the group consisting of an ellipse, an ellipsoid, a circle, a sphere, a rectangle, and a cuboid.

7. A method as claimed in claim 1 comprising displaying, as said screen representation of said control tool, a region of said anatomical image exposure that is associated with said action.

8. A method as claimed in claim 1 wherein the step of varying at least one of said screen representation of said control tool and said speed of movement of said screen representation of said control tool comprises varying at least one of said screen representation of said control tool and said speed of movement of said screen representation of said control tool dependent on forces selected from the group consisting of forces actually acting on an anatomical region associated with said action, forces virtually acting on an anatomical region associated with said action, forces actually emanating from an anatomical region associated with said action, and forces virtually emanating from an anatomical region associated with said action.

9. A method as claimed in claim 8 comprising varying at least one of said screen representation of said control tool and said speed of movement of said screen representation of said control tool dependent on forces occurring in a medical procedure selected from the group consisting of an elastography measurement of tissue in said anatomical image exposure and palpitation of tissue in said anatomical image exposure.

10. A method as claimed in claim 1 wherein the step of varying at least one of said screen representation of said control tool and said speed of movement of said speed representation of said control tool comprises varying said screen representation of said control tool dependent on a location thereof on said display screen.

11. A method as claimed in claim 1 wherein the step of varying at least one of said screen representation of said control tool and said speed of movement of said screen representation of said control tool comprises varying said speed of movement of said screen representation of said control tool dependent on a location of said screen representation of said control tool on said display screen.

12. A method as claimed in claim 1 comprising varying at least one of said screen representation of said control tool and said speed of movement of said screen representation of said control tool continuously.

13. A method as claimed in claim 1 comprising varying at least one of said screen representation of said control tool and said speed of movement of said screen representation of said control tool in steps.

14. A method as claimed in claim 1 wherein the step of varying at least one of said screen representation of said control tool and said speed of movement of said screen representation of said control tool comprises varying said speed of movement of said screen representation of said control tool dependent on a magnitude of measurement data associated with said action.

15. A method as claimed in claim 1 comprising employing as said measurement data, data selected from the group consisting of proton density data, magnetic resonance relaxation times data, data representing flow speed of fluid in said anatomical image exposure, data representing a flow direction of fluid in said anatomical image exposure, data representing the BOLD effect in said anatomical image exposure, data representing a chemical shift in magnetic resonance data of said anatomical image exposure, data representing magnetization transfer in said anatomical image exposure, data representing diffusion in said anatomical image exposure, data representing perfusion in said anatomical image exposure, data representing relaxivity of tissue in said anatomical image exposure, and data representing elasticity of tissue in said anatomical image exposure.

16. A method as claimed in claim 1 comprising acquiring said anatomical image exposure using an imaging modality, as said medical examination imaging apparatus, selected from the group consisting of a magnetic resonance imaging apparatus, a computed tomography apparatus, an x-ray apparatus, an ultrasound apparatus, and an optical camera apparatus.

* * * * *